US008715982B2

(12) United States Patent
Ying et al.

(10) Patent No.: US 8,715,982 B2
(45) Date of Patent: May 6, 2014

(54) IMMOBILISED ENZYMES

(75) Inventors: Jackie Y. Ying, Singapore (SG); Su Seong Lee, Singapore (SG); Yu Han, Singapore (SG)

(73) Assignee: Agency for Science, Technology and Research, Centros (CH)

( * ) Notice: Subject to any disclaimer, the term of this patent is extended or adjusted under 35 U.S.C. 154(b) by 1389 days.

(21) Appl. No.: 11/885,983

(22) PCT Filed: Mar. 8, 2005

(86) PCT No.: PCT/SG2005/000073
§ 371 (c)(1),
(2), (4) Date: May 1, 2008

(87) PCT Pub. No.: WO2006/096132
PCT Pub. Date: Sep. 14, 2006

(65) Prior Publication Data
US 2008/0241877 A1    Oct. 2, 2008

(51) Int. Cl.
*C12N 11/14* (2006.01)
(52) U.S. Cl.
USPC .......................................................... 435/176
(58) Field of Classification Search
None
See application file for complete search history.

(56) References Cited

U.S. PATENT DOCUMENTS 5,175,311 A    12/1992  Doyle
6,072,081 A     6/2000  Itagaki et al.

FOREIGN PATENT DOCUMENTS

| EP | 0313052 A2 | 4/1989 |
| EP | 0223389 B1 | 7/1991 |
| WO | 9218636 | 10/1992 |
| WO | 2004069406 A1 | 8/2004 |

OTHER PUBLICATIONS

Gamoh, "Enzymatic activities of glucose oxidase immobilized under high pressure conditions." Seibutsu Kogakkaishi, 1998 vol. 76, No. 10, p. 413-418. (translation also provided by the examiner).*
Lefevre et al. "Intrusion and extrusion of water in highly hydrophobic *mesoporous* materials: effect of the pore texture" Colloids and Surfaces A: Physiocochemical and engineering aspects, 2004 vol. 241, 265-272.*
Lefevre et al., "Intrusion and extrusion of water in hydrophobic mesopores." Journal of Chemical physics, Mar. 2004, vol. 120, Issue 10, 4927-4938.*
Qiao et al. "Modeling the kinetics of confined nonwetting flow in a *mesoporous* particle." Physica Script, 2005 vol. 71, 27-30.*
Martin et al, "Dissipative water intrusion in hydrophobic MCM-41 type materials" Chemical Communications, 2002, 24-25.*
Gamoh et al, "Evaluation of Activity of Enzyme immobilized under High Pressure Conditions-Activity of immobilized alpha-amylase." Kochi Daigaku Gakujutsu Kenkyo Hokoku, 1996, vol. 45, p. 77-85. (translation also provided by examiner).*
Takahashi H et al, "Catalytic activity in organic solvents and stability of immobilized enzymes depend on the pore size and surface characteristics of *Mesoporous silica*", Chemistry of Materials (2000) 12:3301-3305.*
Yiu HHP et al, "Size selective protein adsorption on thiol-functionalised SBA-15 *mesoporous* molecular sieve", Phys. Chem. Chem. Phys. (2001)3:2983-2985.*
Yiu HHP et al, "Enzyme immobilisation using SBA-15 *mesoporous* molecular sieves with functionalised surfaces", Journa of Mo ecu ar Cata ys s B: Enzymat c (2001) 15:81-92.*
Kevan L et al, "Photoionization of Tetraphenylporphyrin in *Mesoporous* SiMCM-48, AIMCM-48 and TiMCM-48 Molecular Sieves"; Pollution Prevention, The Environmental Institute of Houston, p. 32-33.*
International Search Report for PCT WO 2006/096132 mailed Jun. 6, 2005 (2 pages).
Enzymatic Activities of Glucose Oxidase Immobilized under High-Pressure Conditions, Seibutsu Kogakkaishi, Chemical Abstracts Accession No. 1998:814962, 1998, vol. 76, No. 10, p. 413-418, abstract.
Evaluation of Activity of Enzyme Immobilized under High Pressure Conditions. Activity of immobilized .ALPHA.-amylase, Kochi Daigaku Gakujutsu Kenkyu Hokoku, Shizen Kagaku, Chemical Abstracts Accession No. 1997:369218, (1996) vol. 45, p. 77-85, abstract.
Supplementary European Search Report in counterpart European Application No. 05711230.2 mailed Dec. 30, 2009 (4 pages).
Written Opinion and Search Report issued by the Austrian Patent Office Service and Information Center in counterpart Singapore Application No. 200706498-3 mailed Oct. 6, 2009 (8 pages).
Schmidt-Winkel P. et al, "Microemulsion Templating of Siliceous Mesostructured Cellular Foams with Well-Defined Ultralarge Mesopores", Chemistry of Materials, American Chemical Society, vol. 12, No. 3, Jan. 1, 2000, pp. 686-696 XP002941863 (abstract).
Schmidt-Winkel P. et al, "Mesocellular Siliceous Foams with Uniformly Sized Cells and Windows", Journal of the American Chemical Society, vol. 121, No. 1, Jan. 1, 1999, pp. 254-255, XP002941862.

(Continued)

*Primary Examiner* — Jon P Weber
*Assistant Examiner* — Charles Zoltan Constantine
(74) *Attorney, Agent, or Firm* — Wood, Herron & Evans, LLP (57) ABSTRACT

The present invention relates to a method for immobilizing enzymes in a solid porous support, and to enzymes immobilized in solid porous supports. Specifically, the present invention uses a fluid containing the enzyme under high pressure (such as 25 to 50 Mpa) to immobilize the enzyme (such as CALB) on the porous support (such as silica). The resulting porous support contain more immobilized enzyme than would otherwise have been obtained by a process carried out at atmospheric pressures.

26 Claims, 4 Drawing Sheets

(56) References Cited

OTHER PUBLICATIONS

Han, Yu et al, "Pressure-driven Enzyme Entrapment in Siliceous Mesocellular Foam", Chemistry of Materials, vol. 18, Jan. 2006, pp. 643-649, XP002560431.

http://www.gracedavison.com/eusilica/Adsorbents/product/silica_gel.htm, "Silica Gel", printed Feb. 8, 2005 (2 pages).

Schoemaker HE et al, "Dispelling the Myths—Biocatalysts in Industrial Synthesis", Science (2003) 299:1694-1697.

Straathof AJJ et al, "The production of fine chemicals by biotransformations", Current Opinion in Biotechnology (2002) 13:548-556.

Koeller KM et al, "Enzymes for chemical synthesis", Nature (Jan. 11, 2001) 409:232-240.

Schmid A et al, "Industrial biocatalysis today and tomorrow", Nature (Jan. 11, 2001) 409:258-268.

Levy LM et al, "Resolution of N-protected cis- and trans-3-aminocyclohexanols via lipase-catalyzed enantioselective acylation in organic media", Tetrahedron: Asymmetry (2004) 15:2051-2056.

Gais H-J et al. "Activation of pig liver esterase in organic media with organic polymers. Application to the enantioselective acylation of racemic functionalized secondary alcohols", J. Org. Chem. (2001) 66:3384-3396.

Morrone R et al, "Resolution of racemic acids by irreversible lipase-catalyzed esterification in organic solvents", Eur. J. Org. Chem. (2001) 1441-1443.

Cordova a et al, "A highly chemo- and stereoselective synthesis of β-keto esters via a polymer-supported lipase catalyzed transesterfication", J. Org. Chem. (2001) 66:1906-1909.

Kamal A et al, "A facile preparation of (±)-β-hydroxy nitriles and their enzymatic resolution with lipases", Tehtrahedron: Asymmetry (2001) 12:405-410.

Heiss L et al, "Polyethylene glycol monomethyl ether-modified pig liver esterase: Preparation, characterization and catalysis of enantioselective hydrolysis in water and acylation in organic solvents", Tetrahedron Letters (1995) 36:3833-3836.

Ohya Y et al, "Polycondensation of α-hydroxy acids by enzymes or PEG-modified enzymes in organic media", Journal of Macromolecular Science—Pure Applied Chemistry (1995) A32:179-190.

Tor R et al, "Enzymatically catalysed transesterifications of acryl and methacryl monomeric esters", Enzyme Microb. Technol. (1990) 12:299-304.

Mitchell DT et al, "Smart nanotubes for bioseparations and biocatalysis", J. Am. Chem. Soc. (2002) 124:11864-11865.

Kumar CV et al, "Nanoencapsulation of cytochrome c and horseradish peroxidase at the galleries of alpha-zirconium phosphate", Chemistry of Materials (1997) 9:863-870.

Corma A et al "Electrostatic and covalent immobilsation of enzymes on ITQ-6 delaminated zeolitic materials", Chemical Communications (2001) 419-420.

Wang P et al, "Enzyme stabilization by covalent binding in nanoporous sol-gel-glass for nonaqueous biocatalysis", Biotechnology and Bioengineering (2001) 74:249-255.

Blanco RM et al, "Functionalization of *Mesoporous silica* for lipase immobilization Characterization of the support and the catalysts", Journal of Molecular Catalysis B: Enzymatic (2004) 30:83-93.

Dumitriu E et al, "Preparation and properties of lipase immobilized on MCM-36 support", Journal of Molecular Catalysis B: Enzymatic (2003) 22:119-133.

He J et al, "A new support for the immobilization of penicillin acylase", Journal of Molecular Catalysis B: Enzymatic (2000) 11:45-53.

Lettow JS et al, "Hexagonal to mesocellular foam phase transition in polymer-templated *Mesoporous silicas*", Langmuir (2000) 16:8291-8295.

Fan J et al, "Cubic *Mesoporous silica* with large controllable entrance sizes and advanced adsorption properties", Angew. Chem. Inter. Ed. (2003) 42:3146-3150.

Examination Report in counterpart EP Application No. 05711230.2 dated Apr. 4, 2011 (4 pages).

Brady et al, "Lipase Immoblized on a Hydrophobic, Microporous Support for the Hydrolysis of Fats", JAOCS, vol. 65, No. 6 (Jun. 1988) (pp. 917-921).

Bosley et al, "Blueprint for a Lipase Support: Use of Hydrophobic Controlled-Pore Glasses as Model Systems", Biotechnology and Bioengineering, vol. 43, 1994 (pp. 934-938).

Official Action with Supplementary Search Report issued in corresponding Malaysian Application No. PI 20060979, mailed on Aug. 15, 2012 (7 pages).

\* cited by examiner

IMMOBILISED ENZYMES

TECHNICAL FIELD

The present invention relates to a method for immobilizing enzymes in a solid porous support, and to enzymes immobilized in solid porous supports.

BACKGROUND OF THE INVENTION

Enzyme-catalyzed asymmetric reactions have emerged as one of the most important fields in organic and pharmaceutical synthesis. The kinetic resolution of racemic mixtures is still the most common way to get enantiomerically pure compounds on industrial scales and in academic research. Through kinetic resolution, one enantiomer of a racemic mixture is selectively reacted, whereas the other remained unreacted due to differences in transformation rates.

Immobilization of enzymes on solid supports makes them more mechanically robust, thermally stable, and easily separated from the reaction media. The catalyst activity may also be enhanced when enzymes are immobilized due to reduced enzyme aggregation, especially in non-polar organic media. Polymers and inorganic supports are typically used for immobilizing enzymes. Both covalent bonding and non-covalent interaction have been used for enzyme immobilization. The interaction between the enzyme and the support surface has a significant effect on the enzyme loading, catalyst activity, and stability against enzyme leaching during reaction.

Research has been conducted on enzyme immobilization onto mesoporous silica, mostly via physical adsorption. Porous, hydrophobic silica materials are good candidates as supports for immobilized enzymes since their hydrophobicity may facilitate the access of substrates to the entrapped enzymes within their pores. In addition, the weak hydrophobic interaction between enzyme and support allows the former to maintain its active conformation, leading to high activity. However, there still exist some challenges in the immobilization of enzymes onto hydrophobic porous silica. Conventionally, the immobilization involves stirring porous silica support with the enzyme stock. Relatively low enzyme loading is generally achieved due to the low affinity of aqueous enzyme stock solution with the hydrophobic silica support. The leaching of enzymes from the support is another problem associated with the conventional method. Blanco et al (Blanco, R. M.; Terreros, P.; Fernandez-Perez, M.; Otero, C.; Diaz-Gonzalez, G. *J. Mol. Catal. B: Enzym.* 2004, 30, 83) has reported that leaching of lipase from a hydrophobic mesoporous silica is not likely in anhydrous media, and the immobilized lipase remains active for 15 reaction cycles in acylation of ethanolamine with lauric acid. However, the period of each cycle is only one hour. If stirred for a longer time in anhydrous organic solvent, leaching of enzymes would be likely to occur.

There is therefore a need for a method for immobilizing an enzyme on and/or in a solid support such that leaching of the enzyme from the support is reduced. The method would preferably provide high reactivity of the enzyme and improved thermal stability of the enzyme relative to unimmobilised enzyme.

OBJECT OF THE INVENTION

It is an object of the present invention to overcome or substantially ameliorate at least one of the above disadvantages. It is a further object to at least partially satisfy the above need.

SUMMARY OF THE INVENTION

In a first aspect of the invention there is provided a process for immobilizing a biological species in and/or on a porous support comprising passing a fluid comprising the biological species through the porous support under high pressure.

The high pressure may be greater than about 10 MPa, and may be between about 25 and 50 MPa. The process may comprise recycling the liquid through the porous support under the high pressure. The biological species may be a protein, a protein fragment, a saccharide, a DNA fragment, a peptide or a combination of two or more of these. The biological species may be an enzyme. The fluid comprising the biological species may be a liquid, and may be an aqueous liquid, and may be an aqueous solution. The porous support may be an inorganic porous support, and may comprise silica, or may comprise a metal, or a metal oxide or a mixed metal oxide. The metal may be for example iron, titanium, zirconium or aluminium. The porous support may be a foam, for example an open celled foam, or may be sintered or otherwise porous. It may be mesostructured cellular foam (MCF) or FDU-12. The porous support may be mesoporous. It may have a mean pore size of between about 2 and 50 nm. The porous support may be particulate, and may have a mean particle size between about 100 nm and 200 microns. It may have a narrow particle size distribution. The porous support may be hydrophobic. The process may comprise the step of chemically modifying the porous support, and may comprise hydrophobing the porous support (i.e. rendering it hydrophobic) before passing the liquid comprising the biological species therethrough. The step of chemically modifying (e.g. hydrophobing) may comprise exposing the porous support to a chemical modifying agent (e.g. a hydrophobing agent), for example an alkylsilane, and may comprise exposing the porous support to a solution, a suspension, an emulsion or a dispersion of the chemical modifying agent. The porous support may be dried before passing the liquid therethrough.

The process may additionally comprise one or more of the steps of:
   washing the porous support with an organic washing liquid after the step of chemically modifying,
   washing the porous support with an aqueous washing liquid after the step of chemically modifying,
   drying the porous support after the step of chemically modifying, optionally after one or both of the steps of washing,
   washing the porous support with an organic washing liquid after the step of passing the fluid comprising the biological species therethrough,
   washing the porous support with an aqueous washing liquid after the step of passing the fluid comprising the biological species therethrough, and
   drying the porous support after the step of passing the fluid comprising the biological species therethrough, optionally after one or both of the steps of washing after the step of passing.

In one embodiment, the process comprises the steps of:
   hydrophobing a porous support,
   drying the porous support, and
   recycling a liquid comprising an enzyme through the porous support under a pressure of greater than 10 MPa.
The porous support may be a porous silica support.

In another embodiment the process comprises the steps of:
   hydrophobing a porous support,
   washing the porous support with an organic washing liquid, washing the porous support with an aqueous washing liquid, drying the porous support, recycling a liquid comprising an enzyme through the porous support under a pressure of greater than 10 MPa, washing the porous support with an organic washing liquid, washing the porous support with an aqueous washing liquid, and drying the porous support.

The porous support may be a porous silica support.

In a second aspect of the invention there is provided a porous support having a biological species immobilized therein and/or thereon, when made by a process comprising immobilizing the biological species in and/or on the porous support according to the first aspect of the invention. The porous support may have greater than about 50 mg of biological species per gram of support immobilized therein, and may have between about 50 and 300 mg of biological species per gram of support immobilized therein. The biological species may be a protein, a protein fragment, a saccharide, a DNA fragment, a peptide or a combination of two or more of these. It may be an enzyme. The porous support having the biological species immobilized therein may be thermally stable, and may show no substantial loss in activity after being maintained at 15 hours at 80° C. The porous support having the biological species immobilized therein may be recyclable, and may show a loss of activity of less than about 20% after 8 sequential reuses.

In one embodiment there is provided a hydrophobic mesoporous silica support having an enzyme immobilized therein, when made by a process comprising:

hydrophobing a silica support, drying the silica support, and recycling an aqueous liquid comprising the enzyme through the silica support under a pressure of greater than 10 MPa.

The invention also provides a porous support having a biological species immobilized therein and/or thereon, wherein the porous support has greater than about 50 mg of biological species per gram of support immobilized therein and/or thereon. The porous support may have a higher loading of biological species immobilized therein and/or thereon than the porous support having the biological species immobilized therein and/or thereon by a process performed at atmospheric pressure. It may have a reduced rate of leaching of the biological species than it would have if it were loaded with the biological species under atmospheric pressure. The biological species may be a protein, a protein fragment, a saccharide, a DNA fragment, a peptide or a combination of two or more of these. It may be an enzyme. The porous support may be an inorganic porous support, and may comprise silica, or may comprise a metal, or a metal oxide or a mixed metal oxide. The metal may be for example, iron, titanium, zirconium or aluminium. The porous support may be a foam, for example open celled foam, or may be sintered or otherwise porous. It may be mesostructured cellular foam (MCF) or FDU-12. The porous support may be mesoporous. It may have a mean pore size of between about 2 and 50 nm. The porous support may be particulate, and may have a mean particle size between about 100 nm and 200 microns. It may have a narrow particle size distribution. The porous support may be hydrophobic.

In a third aspect of the invention there is provided a method for catalyzing a chemical reaction comprising exposing a starting material to a porous support having a biological species immobilized therein, wherein the biological species comprises an enzyme capable of catalyzing the reaction of the starting material to produce a product. The porous support having a biological species immobilized therein may be made by a process comprising immobilizing the biological species in and/or on the porous support according to the first aspect of the present invention. It may have greater than about 50 mg of biological species per gram of support immobilized therein and/or thereon. The porous support may have a higher loading of biological species immobilized thereon than the porous support would have if it were loaded with the biological species under atmospheric pressure. The product may be a chiral product, and may have an enantiomeric excess (ee) of greater than about 95%. The chemical reaction may be an asymmetric or enantioselective chemical reaction. The method may be conducted whereby the starting material is in solution. The method may comprise passing the solution through the porous support, and may comprise passing the solution through the porous support at a rate such that the starting material has sufficient time to react to produce the product. The method may comprise suspending, stirring or otherwise distributing the porous support in the solution. It may additionally comprise allowing sufficient time for the starting material to react to produce the product. The sufficient time may depend on the nature of the biological entity, the starting material and the reaction. It may be for example between about 10 minutes and 24 hours. The solution may also comprise a reagent, said reagent being capable of reacting with the starting material under the influence of the biological species to produce the product.

The method may also comprise one or more of:

separating the porous support from the solution, washing the porous support, drying the porous support, and separating the product from the solution.

The steps of washing and drying the porous support may enable reuse of the porous support in subsequent reactions. The step of washing may comprise one or more individual washing steps, and each individual washing step may use different washing liquids. Each washing liquid may, independently, be aqueous or organic. The porous support may or may not be dried between any two individual washing steps.

In an embodiment, there is provided a method for catalyzing a chemical reaction comprising:

exposing a solution comprising a starting material and a reagent to a porous support having a biological species immobilized therein, allowing sufficient time for reaction of the starting material and the reagent, separating the porous support from the solution, and separating a product from the solution, wherein the biological species comprises an enzyme capable of catalyzing the reaction of the reagent and the starting material to produce the product. The porous support having the biological species immobilized therein may be made by a process comprising immobilizing the biological species in and/or on the porous support according to the first aspect of the present invention. The invention also provides a product when produced by the chemical reaction catalysed by the method of the third aspect.

In a fourth aspect of the invention there is provided a reactor (for example a packed bed reactor) for converting a starting material to a product comprising a porous support having a biological species immobilized therein according to the process of the first aspect of the invention, said porous support being disposed within a housing. The biological species may be capable of converting the starting material to the product. The housing may comprise for example an HPLC column housing, a pressure housing, a pressure vessel or some other suitable type of housing. It may comprise a restraining device for preventing the porous support from exiting the housing. The restraining device may be porous, and may be a frit, a filter or some other porous device known in the art of HPLC column manufacture.

The invention also provides for a reactor according to the fourth aspect of the invention when used for converting a starting material into a product.

In a fifth aspect of the invention there is provided a process for preparing a reactor for converting a starting material to a product (for example a reactor according to the fourth aspect of the invention) comprising at least partially filling a housing with a porous support having a biological species immobilized therein. The biological species may be capable of converting the starting material to the product. The porous support having the biological species immobilized therein may be according to the second aspect of the invention, or may be made by immobilizing the biological species in the porous support according to the process of the first aspect of the invention. The housing may have means to prevent the porous support from exiting the housing. The means may comprise for example a filter, a frit or some other porous material. The means may have a pore size smaller than the porous support. The means and the housing may be capable of withstanding the pressures used in the reactor. They may be capable of withstanding a pressure of at least 10 MPa. The housing may be for example an HPLC column housing, and the construction thereof may be according to the methods and parameters well known in the art of making HPLC columns, or it may be some other type of housing. The at least partially filling may comprise forming a mixture, for example a slurry or a suspension, of the porous support with a filling liquid and locating the mixture in the housing. The process may also comprise:

increasing the pressure within the housing to a filling pressure passing a second liquid through the housing at the filling pressure; and optionally, reducing the pressure within the housing to atmospheric pressure.

The second liquid may be the same as the filling liquid, or it may be different from the second liquid.

In a sixth aspect of the invention there is provided a process for preparing a reactor for converting a starting material to a product (for example a reactor according to the fourth aspect of the invention) comprising:

at least partially filling a housing with a porous support; and immobilizing a biological species in and/or on the porous support by passing a liquid comprising the biological species through the porous support under high pressure.

The step of immobilizing may be conducted according to the process of the first aspect of the invention. The biological species may be capable of converting the starting material to the product. The housing may be as described for the fifth aspect of the invention.

The invention also provides a reactor for converting a starting material to a product when made by the process of the fifth or sixth aspect of the invention. It further provides a method for converting a starting material to a product comprising passing the starting material through a reactor according to the fourth aspect of the invention, or a reactor made by the process of the fifth or sixth aspect of the invention.

BRIEF DESCRIPTION OF THE DRAWINGS

A preferred form of the present invention will now be described by way of example with reference to the accompanying drawings wherein.

DETAILED DESCRIPTION OF THE PREFERRED EMBODIMENTS

The present specification discloses a novel pressure-driven method to entrap or immobilise enzymes or other biological entities within the pores of a solid support (matrix), such as a mesoporous silica support modified with hydrophobic silanes. The leaching and thermal stability of the immobilized enzymes have been examined. The solid support may comprise cell-like mesopores connected by windows of a smaller size. A solid support having a suitable pore size may be used. The suitable pore size may depend on the size of biological material, so that the biological species fits into the cell-like mesopores of the solid support. In the case of MCF, the pore sizes (window pore size and cell pore size) may be readily controlled during its synthesis.

The process of the present invention comprises passing a biological species through a porous support, optionally recycling the species through the porous support, under high pressure. The high pressure may depend for example on the particle size and pore size of the porous support. It may be greater than about 10 MPa, and may be greater than about 15, 20, 25, 30, 35, 40, 45 or 50 MPa, and may be between about 10 and 50, 20 and 50, 30 and 50, 40 and 50, 10 and 40, 10 and 30, 10 and 20, 20 and 40 or 20 and 30 MPa, and may be about 10, 15, 20, 25, 30, 35, 40, 45 or 50 MPa. The passing, or recycling, may be for a period of at least 30 minutes, or at least 1, 1.5, 2, 2.5, 3, 3.5, 4, 4.5 or 5 hours, and may be for between about 0.5 and 5 hours, or between about 0.5 and 2, 0.5 and 1, 1 and 5, 2 and 5 or 1 and 3 hours, and may be for about 1, 1.5, 2, 2.5, 3, 3.5, 4, 4.5 or 5 hours. A low temperature such as 0° C. may be used during the passing or recycling. This may be useful where the biological species is unstable. The low temperature may be between about 0 and 15° C., or between about 0 and 10, 0 and 5, 5 and 10 or 10 and 15° C., and may be about 0, 5, 10 or 15° C. The biological species may be a protein, a protein fragment, a saccharide, an enzyme, a DNA fragment, a peptide or a combination of two or more of these. The biological species may be in a fluid, and the fluid may be a liquid, for example an aqueous liquid, and may be dissolved, suspended, emulsified or dispersed in the fluid. The concentration of the biological species in the fluid will depend on the nature of the biological species. The concentration may be between about 1 and 50 mg/ml, or between about 1 and 25, 1 and 10, 1 and 5, 5 and 50, 10 and 50, 25 and 50, 5 and 25 or 5 and 10 mg/ml, and may be about 1, 2, 3, 4, 5, 6, 7, 8, 9, 10, 15, 20, 25, 30, 35, 40, 45 or 50 mg/ml. The fluid may also comprise other species, for example, salts, buffers, nutrients etc. The pH of the fluid may depend on the nature of the biological species, and should be such that the biological species is stable. It may have a pH between about 2 and 9, or between about 2 and 7, 2 and 5, 4 and 9, 7 and 9 or 4 and 7, and may have a pH of about 2, 3, 4, 5, 6, 7, 8 or 9. The biological species may be passed through, or recycled through, the porous support at a temperature that does not denature or degrade the biological species and will depend on the nature of the biological species.

A porous support having a biological species immobilized thereon according to the present invention may have greater than 50 mg biological species per gram of porous support, or greater than 75, 100, 125, 150, 175, 200, 225, 250, 275 or 300 mg/g, and may have between about 50 and 300 mg/g, or between about 100 and 300, 150 and 300, 200 and 300, 250 and 300, 50 and 250, 50 and 100, 100 and 250 or 150 and 200 mg/g, and may have about 50, 75, 100, 125, 150, 175, 200, 225, 250, 275 or 300 mg/g. The porous support may have a higher loading of biological species immobilized thereon than the porous support would have if it were loaded with the biological species under atmospheric pressure. It may be at least about 10% higher, or at least about 15, 20, 25, 30, 35, 40, 45, 50, 55, 60, 65, 70, 75, 80, 85, 90, 95 or 100% higher than the porous support would have if it were loaded with the biological species under atmospheric pressure. It may for example be about 10, 15, 20, 25, 30, 35, 40, 45, 50, 55, 60, 65, 70, 75, 80, 85, 90, 95, 100, 110, 120, 130, 140 or 150% higher than the porous support would have if it were loaded with the biological species under atmospheric pressure. The biological species may be physically adsorbed into and/or onto the porous support.

The porous support may be mesoporous. It may have a mean pore size of between about 2 and 50 nm or between about 10 and 40, 10 and 30, 10 and 20, 20 and 50, 30 and 50, 40 and 50, 20 and 40 or 20 and 30 nm, and may have a mean pore size about 10, 15, 20, 25, 30, 35, 40, 45 or 50 nm. The porous support may be an inorganic porous support, and may comprise silica, or a metal, or a metal oxide or mixed metal oxide. The metal may be for example iron, titanium, zirconium or aluminium. The porous support may be a foam, for example open celled foam, or may be sintered or otherwise porous. It may be mesostructured cellular foam (MCF) or FDU-12, as described in Schmidt-Winkel et al, *Science*, 1999, 548, Lettow et al, *Langmuir*, 2000, 16, 8291 and Fan et al, *Angew. Chem. Int. Ed.*, 2003, 42, 3146. It may be a silica foam according to the copending application entitled "Mesocellular Foam Particles". The porous support may be particulate, for example microparticulate or nanoparticulate, and may have a particle size between about 100 nm and 200 microns. The particle size may be between about 500 nm and 200 microns, or between about 1 and 200, 10 and 200, 50 and 200, 100 and 200, 1 and 100, 1 and 50 or 1 and 10 microns or between about 100 nm and 100 microns, 100 nm and 10 microns, 100 nm and 1 micron or 500 nm and 1 micron, and may be about 100, 200, 300, 400, 500, 600, 700, 800 or 900 microns, or about 1, 2, 3, 4, 5, 6, 7, 8, 9, 10, 20, 30, 40, 50, 60, 70, 80, 90, 100, 110, 120, 130, 140, 150, 160, 170, 180, 190 or 200 microns. The porous support may have a narrow particle size distribution. There may be less than about 50% of particles having a particle size more than 10% different from (greater than or less than) the mean particle size, or there may be less than about 45, 40, 35, 30, 25, 20, 15, 10 or 5% of particles having a particle size more than 10% different from the mean particle size, and may be about 1, 2, 3, 4, 5, 10, 15, 20, 25, 30, 35, 40, 45 or 50% of particles having a particle size more than 10% different from the mean particle size. The particles of the porous support may for example comprise cell-like mesopores connected by windows of a smaller size. The ratio of the size of the mesopores and the size of the windows may be between about 10:1 and 1.5:1, or between about 10:1 and 2:1, 10:1 and 5:1, 5:1 and 1.5:1, 3:1 and 1.5:1, 5:1 and 3:1 or 8:1 and 4:1, and may be about 10:1, 9:1, 8:1, 7:1, 6:1, 5:1, 4.5:1, 4:1, 3.5:1, 3:1, 2.5:1, 2:1 or 1.5:1, or may be some other ratio. The particles of the porous support may have some other structure. It should be understood that when reference is made to the "pore size" of such materials, it refers to the effective pore size, i.e. the size of the narrowest portion of a flow channel through the material. Thus in a structure comprising cell-like mesopores connected by windows of a smaller size, the "pore size" refers to the size of the windows, and not to the size of the mesopores. The particles may have a pore volume between about 0.5 and 5 cm$^3$/g, and may have a pore volume between about 0.5 and 2, 0.5 and 1, 1 and 5, 3 and 5 or 1 and 3 cm$^3$/g, and may have a pore volume between about 0.5, 1, 1.5, 2, 2.5, 3, 3.5, 4, 4.5 or 5 cm$^3$/g. They may have a void volume of between about 50 and 90%, or between about 50 and 70, 60 and 70, 70 and 80, 80 and 90 or 75 and 85%, and may have a void volume of about 50, 55, 60, 65, 70, 75, 80, 85 or 90%. They may have a bulk density of between about 0.2 and 1 g/ml, or between about 0.5 and 1, 0.2 and 0.5, 0.2 and 0.4, 0.2 and 0.3, 0.3 and 0.4 or 0.25 and 0.35 g/ml. and may have a bulk density of about 0.2, 0.25, 0.3, 0.35, 0.4, 0.45, 0.5, 0.55, 0.6, 0.65, 0.7, 0.75, 0.8, 0.85, 0.9, 0.95 or 1 g/ml.

The support may be a hydrophobic support. The process may comprise the step of hydrophobing the porous support. The step of hydrophobing may comprise exposing the porous support to a hydrophobing agent. The hydrophobing agent may be in solution, and may be dissolved in a solvent. The hydrophobing agent may have a group capable of reacting with the porous support, and may also have at least one hydrophobic group. For example, if the porous support comprises silica, then the hydrophobing agent may comprise a hydrolysable group, such as a chlorosilyl group, an alkoxysilyl group, a silazane group or some other suitable group. The hydrophobic agent may be a silane, for example a halosilane, a silazane or an alkoxysilane or some other type of hydrolysable silane (such as an acetoxysilane, an oximosilane, an amidosilane etc.). The hydrophobic group may be an alkyl group, for example C1 to C24 alkyl or bigger than C24 alkyl, or an aryl group, for example C6 to C12 aryl, or some other suitable hydrophobic group. The alkyl group may be straight chain or branched chain, and may have between 1 and 24 carbon atoms, or between 1 and 18, 1 and 12, 1 and 6, 6 and 24, 12 and 24 or 6 and 18 carbon atoms, and may have 1, 2, 3, 4, 5, 6, 7, 8, 9, 10, 11, 12, 14, 16, 18, 20, 22 or 24 carbon atoms. It may comprise a cycloalkyl group such as cyclopentyl, cyclohexyl or cycloheptyl. The aryl group may be for example phenyl, biphenyl, naphthyl or some other aryl group. The aryl or alkl group may be fluorinated or polyfluorinated or perfluorinated. The hydrophobing agent may have one, two, three or more than three hydrophobic groups per molecule. It may for example have a formula $R_nSiX_{4-n}$ or $RMe_2SiCl$, where R is the hydrophobic group, X is the hydrolysable group and n is 1, 2 or 3. Alternatively the hydrophobing agent may comprise a siloxane or a cyclosiloxane. Suitable hydrophobing agents may include chlorodimethyloctylsilane, chlorodimethyloctadecylsilane, methoxytrimethylsilane, dimethyldimethoxysilane, hexamethyldisilazane, hexamethyldisiloxane, decamethylcyclopentasiloxane (D5) or other cyclosiloxanes. The process of hydrophobing may comprise exposing the porous support to the hydrophobing agent, optionally together with a catalyst, for between about 1 and 48 hours, for example between 1 and 24, 1 and 12, 12 and 48, 24 and 48 or 12 and 36 hours (e.g. for about 1, 2, 3, 4, 5, 6, 12, 18, 24, 30, 36, 42 or 48 hours) at a temperature between about 10 and 80° C. The temperature may be between about 10 and 60, 10 and 40, 10 and 20, 20 and 80, 40 and 80, 60 and 80, 20 and 60 or 40 and 60° C., and may be about 10, 20, 30, 40, 50, 60, 70 or 80° C. The catalyst may depend on the nature of the hydrophobing agent and of the porous support. It may be for example an amine, such as a tertiary amine, and may be for example trimethylamine or triethylamine, pyridine or some other base. The hydrophobing agent and, if present, the catalyst, may be dissolved in a solvent. The solvent may be organic, and may be non-hydroxylic, and may be for example toluene, xylene or some other suitable solvent. The exposing may comprise immersing the porous support in a solution of the hydrophobing agent in the solvent, and may comprise stirring, swirling, shaking, sonicating or otherwise agitating the solution with the porous support therein, or it may comprise passing the solution through the porous support, and optionally recirculating the solution through the porous support. The present invention also envisages other types of chemical modification which may be appropriate depending on the nature of the porous support and the biological species.

The porous support may be degassed and/or dried before being chemically modified or hydrophobed. It may be heated to a temperature between about 100 and 200° C., for example between 100 and 150, 100 and 120, 150 and 200, 170 and 200 or 125 and 175° C. (e.g. about 100, 110, 120, 130, 140, 150, 160, 170, 180, 190 or 200° C.). It may have heated, and optionally dried, gases passed therethrough at a temperature as listed above. It may have gases, optionally dried gases, passed therethrough at atmospheric temperature. It may be exposed to a vacuum at a temperature as listed above. The vacuum may have an absolute pressure of less than about $10^{-2}$ torr, or less than about $5*10^{-3}$, $10^{-3}$, $5*10^{-4}$, $10^{-4}$, $5*10^{-5}$, $10^{-5}$, $5*10^{-6}$ or $10^{-6}$ torr, and may have an absolute pressure of between about $10^{-2}$ and $10^{-6}$ torr, or between about $10^{-3}$ and $10^{-6}$ torr, $10^{-4}$ and $10^{-6}$ torr, $10^{-5}$ and $10^{-6}$ torr, $10^{-3}$ and $10^{-5}$ torr or $10^{-4}$ and $10^{-5}$ torr, and may have a pressure of about $5*10^{-3}$, $10^{-3}$, $5*10^{-4}$, $10^{-4}$, $5*10^{-5}$, $10^{-5}$, $5*10^{-6}$ or $10^{-6}$ torr.

After being chemically modified (e.g. hydrophobed), the porous support may be washed one or more times. Each wash may be with a different washing solvent, or some of the washes may be with the same solvent. The solvent may be aqueous or may be organic. The organic solvent may be polar or non-polar. Suitable solvents include water, methanol, ethanol, isopropanol, acetone, dichloromethane, ethyl acetate, toluene and xylene, and may also be any miscible combination of suitable solvents. After any or all of the washes the porous support may be dried. The drying may comprise for example heating (for example as described above), passing a gas through the porous substrate, or exposing the porous substrate to a vacuum (for example as described above). The gas may be air, nitrogen, carbon dioxide or some other gas, and may be heated or may be not heated.

After the step of passing the biological species through the porous support, the porous support may be washed one or more times, as described above. After any or all of the washes the porous support may be dried. The drying may comprise for example heating passing a gas through the porous substrate, or exposing the porous substrate to a vacuum. The gas may be air, nitrogen, carbon dioxide or some other gas, and may be heated or may be not heated. The heating (and/or the heated gas) may employ a temperature that does not degrade or denature the biological species. This will depend on the nature of the biological species. The porous support having the biological entity supported therein may be thermally stable. It may be thermally stable up to a temperature of about 50° C., or up to a temperature of about 60, 70, 80, 90 or 100° C. It may show a loss in catalytic activity of less than about 10%, or less than about 9, 8, 7, 6, 5, 4, 3, 2, or 1% on heating to the temperature for about 15 hours, or about 14, 13, 12, 11, 10, 9, 8, 7, 6 or 5 hours. The heating may be in air or in some inert gas, for example nitrogen or carbon dioxide, or it may be in a vacuum.

A porous support according to the present invention, having a biological species immobilized therein, may be used to catalyse a chemical reaction of a starting material to a product. The chemical reaction may be one which may be catalysed by the biological species. It may be an asymmetric reaction and may be a reaction that generates a chiral product. The enantiomeric excess of the chiral product may be greater than about 95%, or greater than about 96, 97, 98, 99, 99.5, 99.6, 99.7, 99.8 or 99.9, and may be about 95, 96, 97, 98, 99, 99.5, 99.6, 99.7, 99.8, 99.9 or 100%. The enantiomeric excess may be about the same as if the reaction were conducted with the biological species not immobilized in the porous support, or it may be different.

The method of catalyzing the reaction may comprise passing a solution of the starting material in a solvent through the porous support, or it may comprise suspending, stirring or otherwise distributing the porous support in the solution. The solution may also comprise a reagent, said reagent being capable of reacting with the starting material under the influence of the biological species to produce the product. The solvent may be any suitable solvent which is capable of dissolving the starting material and, if present, the reagent. It may be an aqueous solvent or an organic solvent, or a mixture comprising an aqueous and an organic solvent. Suitable solvents include water, methanol, ethanol, isopropanol, acetone, dichloromethane, ethyl acetate, toluene and xylene, and combinations of solvents. Thus the reaction maybe conducted continuously, by passing a stream of starting material in a solvent, optionally together with a reagent, through the porous support. Alternatively it may be conducted batchwise, wherein, for example, a single batch comprises contacting a batch of starting material in a solvent, optionally together with a reagent, with the porous support, allowing sufficient time for reaction. In either case it is important that the starting material be in contact with the porous support for sufficient time for reaction to occur. The sufficient time will depend on the nature of the starting material, of the reaction and of the porous support (for example the loading of biological species in the porous support). The sufficient time may be between about 10 minutes and 24 hours. The sufficient time may be between 10 minutes and 12 hours, 10 minutes and 6 hours, 10 minutes and 3 hours, 10 minutes and 1 hour, 10 and 30 minutes, 1 and 24 hours, 6 and 24 hours, 12 and 24 hours, 18 and 24 hours, 1 and 12 hours or 1 and 6 hours, and may be about 10, 20, 30, 40 or 50 minutes, or about 1, 2, 3, 4, 5, 6, 7, 8, 9, 10, 11, 12, 13, 14, 15, 16, 17, 18, 19, 20, 21, 22, 23 or 24 hours, or may be more than 24 hours. If the reaction is conducted continuously as described above, the flow rate of the solution through the porous support having the biological entity immobilized therein may be sufficient to allow sufficient time for the reaction to occur. Thus the flow rate will be less than or equal to one column length per the sufficient time (as detailed above). The actual flow rate (in ml/min, for example) will therefore depend on the dimensions (particularly the cross-sectional area) of a container (e.g. column) in which the porous support having the biological entity immobilized therein is located. The flow rate may be adjusted, for example, by adjusting the pressure applied to the solvent comprising the starting material.

The method may also comprise one or more of:
separating the porous support from the solution,
washing the porous support,
drying the porous support, and
separating the product from the solution.

The step of separating the porous support may comprise filtering, centrifuging, ultracentrifuging, settling, decanting or a combination of these, or it may comprise some other suitable method. The step of washing may comprise suspending the porous support in a washing solvent, stirring, swirling, shaking, sonicating or otherwise agitating the porous support in a washing solvent, passing a washing solvent through the porous support or any combination of these. The washing solvent may be any suitable solvent, for example water, methanol, ethanol, isopropanol, acetone, dichloromethane, ethyl acetate, toluene and xylene, or it may be a combination of solvents. The step of washing may be conducted several times, and may be conducted using different washing solvents. After each washing step, the porous support may be dried, or it may not be dried. The drying may comprise for example heating, passing a gas through the porous substrate, or exposing the porous substrate to a vacuum. The gas may be air, nitrogen, carbon dioxide or some other gas, and may be heated or may be not heated. The heating (and/or the heated gas) may employ a temperature that does not degrade or denature the biological species. This will depend on the nature of the biological species. A low temperature such as 0° C. may be used during the passing or recycling. This may be useful where the biological species is unstable. The low temperature may be between about 0 and 25° C., or between about 0 and 20, 0 and 15, 0 and 10, 0 and 5, 5 and 10, 10 and 15, 15 and 20, 20 and 25, 5 and 20, 5 and 15 or 10 and 20° C., and may be about 0, 5, 10, 15, 20 or 25° C. The step of separating the product from the solution may be performed using any of the methods known in the art for doing so. These may include, for example, one or more of preparative HPLC, preparative GC, column chromatography, evaporation, distillation, recrystallisation, solvent precipitation or sublimation.

The support with the biological entity immobilized thereon may be reused for multiple batches, i.e. in any one batch (except the first batch) the support with the biological entity thereon may have been used in an earlier reaction. It may be reused for more than 1 batch, or more than 2, 3, 4, 5, 6, 7, 8, 9, 10, 11, 12, 13, 14, 15, 16, 17, 18, 19 or 20 batches. The catalytic activity on any reuse may drop from the original catalytic activity by less than about 20%, or less than about 20, 15, 10 or 5%, and may drop by about 0, 0.1, 0.2, 0.3, 0.4, 0.5, 1, 1.5, 2, 2.5, 3, 4, 5, 10, 15 or 20%.

Experiment
Materials

The support materials were mesostructured cellular foam (MCF) and FDU-12, which were synthesized according to literature (Schmidt-Winkel et al, *Science,* 1999, 548, Lettow et al, *Langmuir,* 2000, 16, 8291 and Fan et al, *Angew. Chem., Int. Ed.,* 2003, 42, 3146). Free enzyme, Candida Antarctica 2 Lipase B (CALB), was purchased from Roche. Novozyme 435 (a commercial immobilized enzyme) was provided by Novo Nordisk. Chlorodimethyloctylsilane and chlorodimethyloctadecylsilane were purchased from Aldrich.

Methods
Chemical Modifications of Mesoporous Materials

Two long-chain alkyl groups, octyl and octadecyl, were used to prepare hydrophobic mesoporous materials. After degassing at 150° C. under vacuum overnight, MCF (3.0 g) was suspended in toluene (40 ml), Triethylamine (12.0 mmol, 1.67 ml) and chlorodimethyloctylsilane (6.0 mmol, 1.42 ml) were then added sequentially under stirring. The suspension was stirred at 60° C. for 24 hr and filtered. The solid was washed with toluene, methanol, acetone and dichloromethane several times, and dried under vacuum. The modified MCF is termed MCF-C8. MCF-C18 was prepared by the same procedure except that chlorodimethyloctadecylsilane (6.0 mmol, 2.08 g) was used instead of chlorodimethyloctylsilane. FDU-12-C8 was also prepared by the same procedure using FDU-12 instead of MCF.

Enzyme Immobilization
Conventional Loading Method

The functionalized MCF (0.6 g) was stirred vigorously in 50 ml of CALB stock solution (8 mg/ml) for 24 hr. The suspension was filtered and washed with distilled water and hexane. After drying under vacuum, the sample was subjected to C, H, N analysis for enzyme loading, based on the proportion of nitrogen in free enzyme. The result was confirmed by measuring the protein amount in the supernatant after immobilization via Bradford assay.

Pressure-Driven Loading Method

The functionalized MCF (0.6 g) was dispersed in cyclohexane and then packed into a high-pressure liquid chromatography (HPLC) column (100 mm×4.6 mm) under a high pressure using a slurry packer. The packed column was fully dried under vacuum. Enzyme stock solution (50 ml, 8 mg/ml) was cycled through the silica column for 2 hr under a high pressure of 5000 psi (about 35 MPa). The enzyme-loaded silica was then collected from the column, washed with distilled water and hexane, and dried under vacuum. The enzyme loading was determined by C, H, N analysis and Bradford assay as described in the previous section.

Catalytic Reaction

Kinetic resolution of 1-phenylethanol acylated with isopropenyl acetate was used to assess the catalytic activity (Scheme 1).

Scheme 1: Kinetic Resolution of 1-Phenylethanol with Isopropenyl Acetate by CALB In a typical procedure, a certain amount of catalyst (containing a fixed total CALB loading of 10 mg) was dispersed in dry toluene (15 ml). 1-phenylethanol (10.8 mmol, 1.34 ml) and isopropenyl acetate (17.4 mmol, 1.58 ml) were then added sequentially at room temperature. The reaction was monitored with gas chromatography (GC) until complete conversion was achieved. The enantiomeric excess (% ee) was then determined by HPLC.

Catalyst Recycling

After the reaction was finished, the catalyst was filtered, washed several times with toluene, and dried under vacuum.

The dried catalyst was reweighed so as to determine the exact amount of substrates to be used in the new reaction cycle.

Pack Bed Reactor

CALB was immobilized onto MCF-C18 by the pressure-driven method using a 250 mm×4.6 mm HPLC column. The column was washed several times with distilled water under a high pressure (2000 psi). It was then dried under vacuum, and used directly as a pack bed reactor, 0.65 M of 1-phenylethanol and 0.97 M of isopropenyl acetate in toluene were flowed through the pack bed reactor. To determine the flow rate for achieving full conversion, the product was continuously analyzed with GC.

Results and Discussion

Characterization of Functionalized MCF

Calcined MCF has well-defined and ultralarge mesopores with a mean pore diameter of 24 nm. Its pore volume and surface area are 2.2 cm$^3$/g and 680 m$^2$/g respectively. The pore diameter can be controlled easily by changing the synthesis condition. The modification of MCF with C$_8$ groups decreased the pore diameter by 2 nm (Table 1). When modified with C$_{18}$ groups, MCF showed a decrease in pore diameter by 4 nm. The surface area and pore volume of MCF-C$_8$ and MCF-C$_{18}$ were also lower than the unmodified MCF (Table 1).

TABLE 1

Characteristics of the CALB-loaded mesoporous silica.

| | Pore Size (nm)/ Window Size (nm) | Pore Volume (cm$^3$/g) | Enzyme loading (mg/g) | |
|---|---|---|---|---|
| | | | by Stirring | by Pressure |
| MCF-C$_8$ | 21.3/12.1 | 1.60 | 92 | 275 |
| MCF-C$_{18}$ | 20.0/10.6 | 1.27 | 65 | 250 |
| FDU-12-C$_8$ | 9.1/3.5 | 0.454 | 30 | 98 |

Enzyme Loading

Compared to the conventional method, the pressure-driven method gave much higher enzyme loading (by 3 to 4 times) on MCF-C$_8$, MCF-C$_{18}$ and FDU-12-C$_8$ in a shorter period of time (Table 1). For example, 24 hour of stirring led to an enzyme loading of 92 mg/g of MCF-C$_8$, whereas an enzyme loading of 275 mg/g MCF-C$_8$ was achieved by the pressure-driven method in just 2 hr. FDU-12-C$_8$, which has smaller pore size and pore volume than MCF-C$_8$, showed a lower enzyme loading than MCF-C$_8$. It also demonstrated a greater enzyme loading by the pressure-driven method than by the conventional method.

Activity and Selectivity in Kinetic Resolution of 1-Phenylethanol

Figure 1:
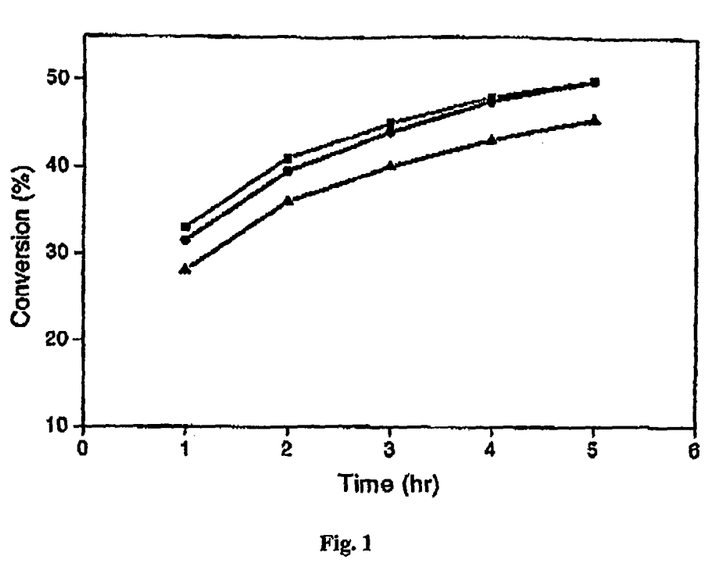
FIG. 1 is a graph showing catalytic activities of CALB/MCF-$C_{18}$ (squares), CALB/MCF-$C_8$ (circles), and free CALB (triangles) in the example.

The acylation of 1-phenylethanol by CALB was performed at room temperature in toluene. CALB/MCF-C$_8$ and CALB/MCF-C$_{18}$ prepared by the pressure-driven method showed similar catalytic activity (see FIG. 1). Under typical reaction conditions (see above: "Catalytic reaction"), complete conversion (i.e. 50% conversion) of (R)-1-phenylethanol to (R)-1-phenylethyl acetate was achieved after 5 hr in both cases. In contrast, free CALB showed a slower reaction rate, giving 45.5% conversion in 5 hr. Free enzyme usually formed aggregates in organic solvents. By loading CALB uniformly within the mesopores of MCF silica, aggregation might be avoided or reduced, giving rise to a greater enzyme catalytic activity. All three catalysts in FIG. 1 demonstrated high enantioselectivities (ee$_g$>99.7% and ee$_p$>99.7%), illustrating that the pressure-driven loading process did not alter the selectivity of CALB. (ee$_g$ refers to the enantioselectivity of the substrate, in other words, remaining reactant, and ee$_p$ stands for the enantioselectivity of the product.)

Enzyme Leaching Over Multiple Reaction Runs

Figure 2:
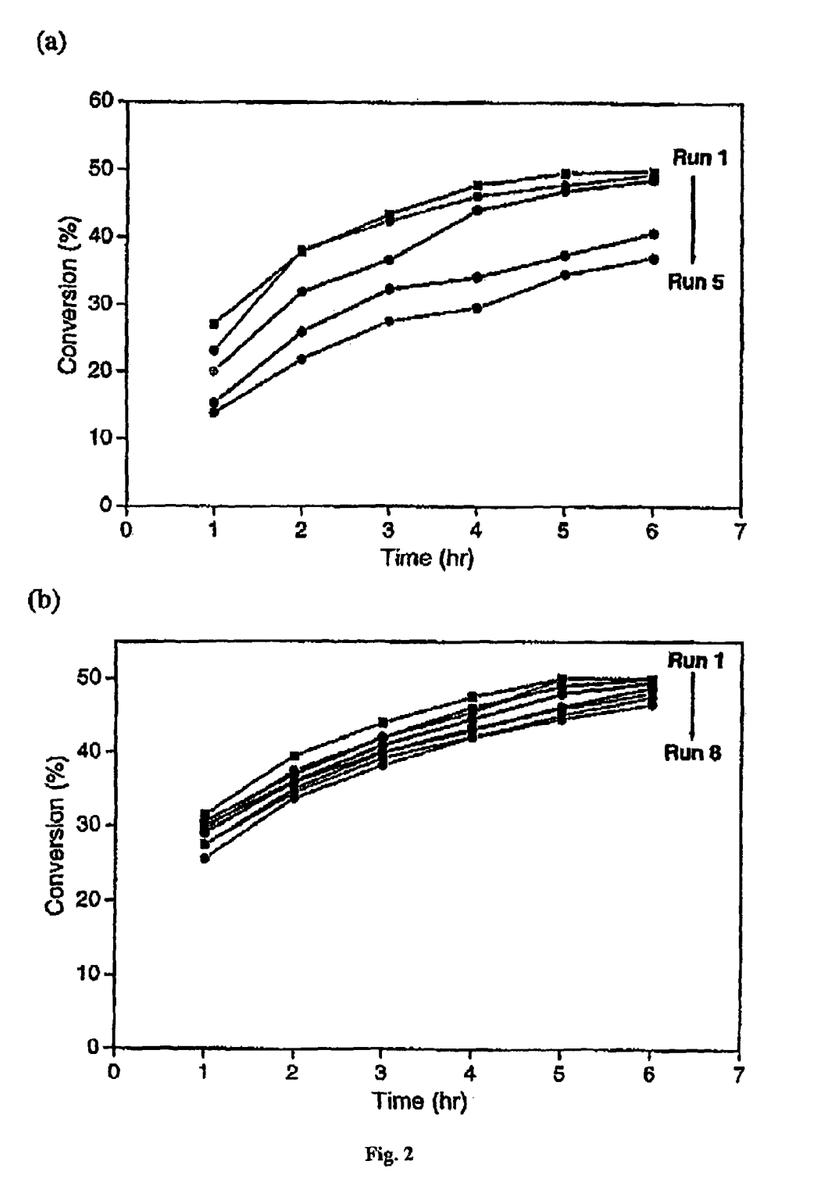
FIG. 2 shows two graphs showing conversion vs. time in sequential runs over CALB/MCF-$C_8$ prepared by (a) the conventional immobilization method, and (b) the pressure-driven method of the present invention.

Any enzyme leaching during reaction would lead to decreased conversions in subsequent runs. It could also be determined quantitatively by C, H, N analysis. CALB/MCF-C$_8$ prepared by the conventional method showed a substantial drop in conversion ((from 50% to 37%) over 5 runs (FIG. 2a). In contrast, CALB/MCF-C$_8$ prepared by the pressure-driven method only showed a minor decrease in conversion (from 50% to 46.5%) after 8 runs or 48 hours of reactions (FIG. 2b). The results of C, H, N analysis indicated that after 5 runs, over 65% of CALB was leached out of MCF-C$_8$ when immobilized by the conventional method (see Table 2).

TABLE 2

Enzyme loading in MCF-C$_8$ over different reaction cycles.

| | Enzyme Content (mg/g) | | |
|---|---|---|---|
| | Before the 1$^{st}$ Cycle | After the 5$^{th}$ Cycle | After the 8$^{th}$ Cycle |
| Conventional Method | 92 | 30 | — |
| Pressure-Driven Method | 275 | — | 250 |

When introduced by the pressure-driven method, CALB mostly remained within the mesoporous support, with only about 10% leaching detected after 8 runs. We note that the pressure-driven method not only improved enzyme loading, but also reduced enzyme leaching.

The enzyme molecules were likely pushed and settled deep within the mesopores of MCF-C$_8$ by the pressure-driven method. In contrast, a substantial amount of the enzyme molecules were probably weakly adsorbed on the outer surface of the support in the conventional stirring method. This would explain the differences in the amount of enzyme leaching from the two immobilization methods.

After the enzymes were loaded by the pressure-driven method, the immobilized enzyme catalysts were washed with distilled water several times. The filtrate from these washes did not contain any enzymes, as determined by the Bradford assay. This also illustrated that the enzymes were firmly entrapped within the mesopores of MCF-C$_8$.

Assessment of Reusability

Figure 3:
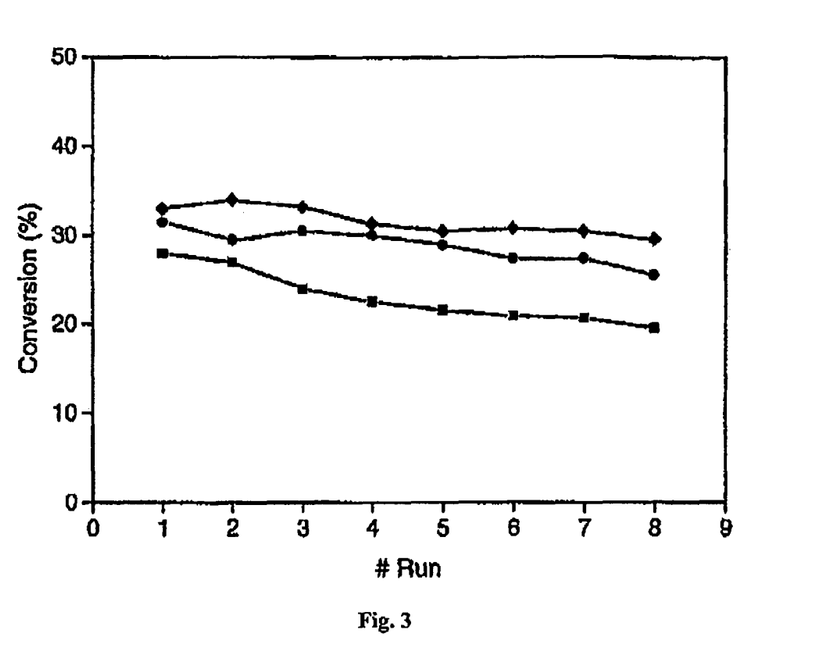
FIG. 3 is a graph showing 1-hour conversions achieved in sequential runs by commercial immobilized CALB (Novozym 435) (squares), CALB/MCF-$C_8$ immobilized by the pressure-driven method of the present invention (circles) and CALB/MCF-$C_{18}$ immobilized by the pressure-driven method of the present invention (diamonds)

The reusability of CALB/MCF-C$_8$ and CALB/MCF-C$_{18}$ prepared by the pressure-driven method was compared to the commercially available Novozyme 435. Compared to Novozyme 435, CALB/MCF-C$_{18}$ and CALB/MCF-C$_8$ showed superior 1-hour conversions over multiple runs (FIG. 3). This study illustrates that enzymes immobilized on mesoporous silica supports by the pressure-driven method have more stable activity than those immobilized in polymer matrix commercially (Novozyme 435).

Thermal Stability

Figure 4:
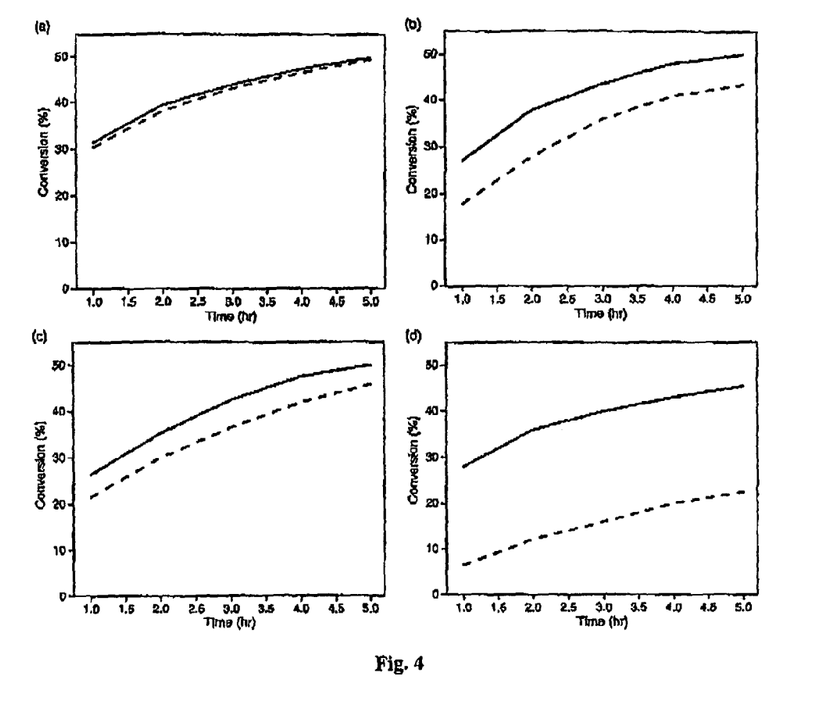
FIG. 4 shows four graphs of the conversion of CALB/MCF-$C_8$ prepared by (a) the pressure driven method of the present invention, (b) the conventional method, (c) Novozym 435, and (d) free CALB, wherein catalysts were tested before (solid lines) and after (dashed lines) thermal treatment.

To examine their thermal stability, free and immobilized CALB catalysts were treated at 80° C. for 15 hr, and then tested with the kinetic resolution reaction. CALB/MCF-C$_8$ prepared by the pressure-driven method did not show any loss in activity from the heat treatment (FIG. 4a). In contrast, CALB/MCF-C$_8$ prepared by the conventional method and Novozyme 435 showed a substantial reduction in activity after the thermal treatment (FIGS. 4b and 4c). Free CALB was severely deactivated upon heat treatment and lost a majority of its activity (FIG. 4d). This study illustrates the need to immobilize the enzyme catalysts to achieve greater thermal stability, and the pressure-driven method is particularly effective at this.

Pack Bed Reactor of CALB/MCF-$C_{18}$

CALB/MCF-$C_{18}$ packed bed reactor was prepared by the pressure-driven method using a 250 mm×4.6 mm HPLC column. Full conversion of (R)-1-phenylethanol to (R)-1-phenylethyl acetate was achieved at a flow rate of 1.5 ml/mm with 0.65 M of 1-phenylethanol and 0.97 M of isopropenyl acetate in toluene. A flow rate below 0.5 ml/min gave white products from the polymerization of isopropenyl acetate by CALB. This polymer product increased the back pressure. The polymerization did not occur under the optimized reaction condition (1.5 ml/mm). The activity and enantioselectivity of the pack bed reactor did not vary during a continuous reaction of 6 hr.

CONCLUSIONS

The novel pressure-driven method of enzyme immobilization greatly enhanced the enzyme loading onto a hydrophobic mesoporous silica support. A very high enzyme loading of up to 280 mg/g of support was achieved. The immobilized enzymes showed less leaching during multiple runs than commercial Novozyme 435. The thermal stability of enzymes was also significantly improved by the novel immobilization approach. CALB/MCF-$C_{18}$ prepared by the pressure-driven method was successfully applied as a packed bed reactor.

This method can be broadly applied to immobilize other enzymes onto mesoporous silica. This study also illustrates MCF as an excellent support for enzyme immobilization. The pore size of MCF can be easily controlled to optimize the loading of enzymes of different sizes.

The invention claimed is:

1. A process for immobilizing an enzyme in a porous support comprising passing a fluid comprising the enzyme through the porous support under high pressure, wherein the porous support is selected from the group consisting of mesostructured siliceous foam (MCF) and FDU-12 and the high pressure immobilizes the enzyme within the porous support.

2. The process of claim 1 wherein the pressure is greater than about 10 MPa.

3. The process of claim 1 wherein the pressure is between about 25 and 50 MPa.

4. The process of claim 1 wherein the porous support has a mean pore size of between about 2 and 50 nm.

5. The process of claim 1 wherein the porous support is hydrophilic.

6. The process of claim 1 wherein the porous support is hydrophobic.

7. The process of claim 1 further comprising a step of hydrophobing the porous support before passing the fluid therethrough.

8. The process of claim 1 further comprising recycling the fluid through the porous support under high pressure.

9. The process of claim 1 further comprising drying the porous support before passing the fluid therethrough.

10. The process of claim 1 wherein the pressure is between about 10 and 50 MPa.

11. The process of claim 1 wherein the fluid is an aqueous liquid.

12. A porous support having an enzyme immobilized therein, when made by a process comprising passing a fluid comprising the enzyme through the porous support under high pressure, wherein the porous support is selected from the group consisting of mesostructured siliceous foam (MCF) and FDU-12 and the high pressure immobilizes the enzyme within the porous support.

13. The porous support of claim 12 said porous support having a mean pore size of between about 2 and 50 nm.

14. The porous support of claim 12, said porous support being hydrophilic.

15. The porous support of claim 12, said porous support being hydrophobic.

16. The porous support of claim 12 wherein the process comprises a step of hydrophobing the porous support before passing the fluid therethrough.

17. The porous support of claim 12 wherein the process comprises recycling the fluid through the porous support under high pressure.

18. The porous support of claim 12 wherein the process comprises drying the porous support before passing the fluid therethrough.

19. A method for catalyzing a chemical reaction comprising exposing a starting material to a porous support having an enzyme immobilized therein, wherein the enzyme is capable of catalyzing the reaction of the starting material to produce a product wherein the porous support having the enzyme immobilized therein is made by a process comprising passing a fluid comprising the enzyme through the porous support under high pressure, wherein the porous support is selected from the group consisting of mesostructured siliceous foam (MCF) and FDU-12 and the high pressure immobilizes the enzyme within the porous support.

20. The method of claim 9 wherein the product is a chiral product.

21. The method of claim 9 wherein the starting material is in solution.

22. The method of claim 21 comprising passing the solution through the porous support having the enzyme immobilized therein.

23. The method of claim 21 wherein the solution also comprises a reagent.

24. The method of claim 19 wherein the porous support having the enzyme immobilized therein has been used in an earlier reaction.

25. A reactor for converting a starting material to a product comprising a porous support having an enzyme immobilized therein by a process comprising passing a fluid comprising the enzyme through the porous support under high pressure, wherein the porous support is selected from the group consisting of mesostructured siliceous foam (MCF) and FDU-12 and the high pressure immobilizes the enzyme within the porous support, said porous support being disposed within a housing.

26. A process for preparing a reactor for converting a starting material to a product comprising at least partially filling a housing with a porous support having an enzyme immobilized therein by a process comprising passing a fluid comprising the enzyme through the porous support under high pressure, wherein the porous support is selected from the group consisting of mesostructured siliceous foam (MCF) and FDU-12 and the high pressure immobilizes the enzyme within the porous support.

* * * * *